(12) United States Patent
Dahlström et al.

(10) Patent No.: US 7,326,724 B2
(45) Date of Patent: Feb. 5, 2008

(54) SALTS OF OMEPRAZOLE AND ESOMEPRAZOLE I

(75) Inventors: Mikael Dahlström, Mölndal (SE); Arne Brändström, Funäsdalen (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/569,819

(22) PCT Filed: Sep. 1, 2004

(86) PCT No.: PCT/SE2004/001258

§ 371 (c)(1),
(2), (4) Date: Feb. 27, 2006

(87) PCT Pub. No.: WO2005/023796

PCT Pub. Date: Mar. 17, 2005

(65) Prior Publication Data

US 2007/0004778 A1   Jan. 4, 2007

(30) Foreign Application Priority Data

Sep. 4, 2003   (SE) .................................. 0302381

(51) Int. Cl.
*A61K 31/4439* (2006.01)
*C07D 401/12* (2006.01)

(52) U.S. Cl. .................................... 514/341; 546/273.7
(58) Field of Classification Search ................ 514/341; 546/273.7
See application file for complete search history.

(56) References Cited

FOREIGN PATENT DOCUMENTS

| EP | 005129 B1 | 4/1981 |
|---|---|---|
| EP | 124495 A2 | 1/1987 |
| WO | WO-94/27988 A1 | 12/1994 |
| WO | WO-96/02535 A1 | 2/1996 |
| WO | WO-97/41114 A1 | 11/1997 |
| WO | WO-98/54171 A1 | 12/1998 |
| WO | WO-03/074514 A1 | 9/2003 |
| WO | WO-05/023797 A1 | 3/2005 |

*Primary Examiner*—Patricia L. Morris
(74) *Attorney, Agent, or Firm*—White & Case LLP

(57) ABSTRACT

The present invention relates to new salts of omeprazole and esomeprazole respectively, i.e. salts of 5-methoxy-2-[[(4-methoxy-3,5-dimethyl-2-pyridinyl)-methyl]sulfinyl]-1H-benzimidazole and the (S)-enantiomer thereof. More specifically, the present invention relates to adamantan ammonium salt of the compounds, formed by a reaction of omeprazole and esomeprazole respectively and adamantan amine. The present invention also relates to a process for preparing the compounds of the invention, a pharmaceutical preparation and a method for treatment of gastric related disorders by administering the compounds of the invention.

13 Claims, 3 Drawing Sheets

SALTS OF OMEPRAZOLE AND ESOMEPRAZOLE I

FIELD OF THE INVENTION

The present invention relates to novel salts of 5-methoxy-2-[[(4-methoxy-3,5-dimethyl-2-pyridinyl)-methyl]sulfinyl]-1H-benzimidazole or salts of the single enantiomers thereof in a pure and isolated form. Specifically, it relates to adamantan ammonium salts of the compounds. The present invention also relates to processes for preparing the adamantan ammonium salts of omeprazole and esomeprazole in a pure and isolated form and pharmaceutical compositions containing them.

BACKGROUND OF THE INVENTION AND PRIOR ART

The compound 5-methoxy-2-[[(4-methoxy-3,5-dimethyl-2-pyridinyl)methyl]sulfinyl]-1H-benzimidazole having the generic name omeprazole, and therapeutically acceptable salts thereof, are described in EP 0 005 129.

Omeprazole is a sulfoxide and a chiral compound, wherein the sulphur atom being the stereogenic center. Thus, omeprazole is a racemic mixture of its two single enantiomers, the (R)- and (S)-enantiomer of omeprazole, herein referred to as (R)-omeprazole and (S)-omeprazole, the latter have the generic name esomeprazole. The absolute configuration of the enantiomers of omeprazole has been determined by an X-ray study of an N-alkylated derivative of the (R)-enantiomer.

Omeprazole and esomeprazole are proton pump inhibitors, and are useful as antiulcer agents. In a more general sense, omeprazole and esomeprazole may be used for prevention and treatment of gastric acid related diseases in mammals and especially in man. Specific alkaline salts of omeprazole are disclosed in EP 0 124 495. Herein, quaternary ammonium salts and guanidine salts of omeprazole are disclosed. Document WO 97/41114 discloses processes for preparing magnesium salt of benzimidazoles, including magnesium salt of omeprazole. However, no salts of omeprazole prepared from primary amines are mentioned in these documents.

Certain salts of the single enantiomers of omeprazole and their preparation are disclosed in WO 94/27988, for instance, quaternary ammonium salts of esomeprazole are mentioned. However, no salts employing primary, secondary or tertiary amines are disclosed or suggested. The described salts of esomeprazole have improved pharmacokinetic and metabolic properties, which will give an improved therapeutic profile such as a lower degree of interindividual variation. WO 96/02535 and WO 98/54171 disclose preferred processes for preparing esomeprazole and salts thereof. Further, primary amine salts are described in WO 03/074514.

In the formulation of drug compositions, it is important for the active pharmaceutical ingredient to be in a form in which it can be conveniently handled and processed. This is of importance, not only from the point of view of obtaining a commercially viable manufacturing process, but also from the point of view of subsequent manufacture of pharmaceutical formulations (e.g. oral dosage forms such as tablets) comprising the active pharmaceutical ingredient.

Further, in the manufacture of oral pharmaceutical compositions, it is important that a reliable, reproducible and constant plasma concentration profile of the active pharmaceutical ingredient is provided following administration to a patient.

Chemical stability, solid state stability, and "shelf life" of the active pharmaceutical ingredient are important properties for a pharmaceutical active compound. The active pharmaceutical ingredient, and compositions containing it, should be capable of being effectively stored over appreciable periods of time, without exhibiting a significant change in the physico-chemical characteristics of the active pharmaceutical ingredient, e.g. its chemical composition, density, hygroscopicity and solubility. Thus, in the manufacture of commercially viable and pharmaceutically acceptable drug compositions, it is important, wherever possible, to provide the active pharmaceutical ingredient in a crystalline and stable form.

DRAWINGS

DESCRIPTION OF THE INVENTION

Figure 1:
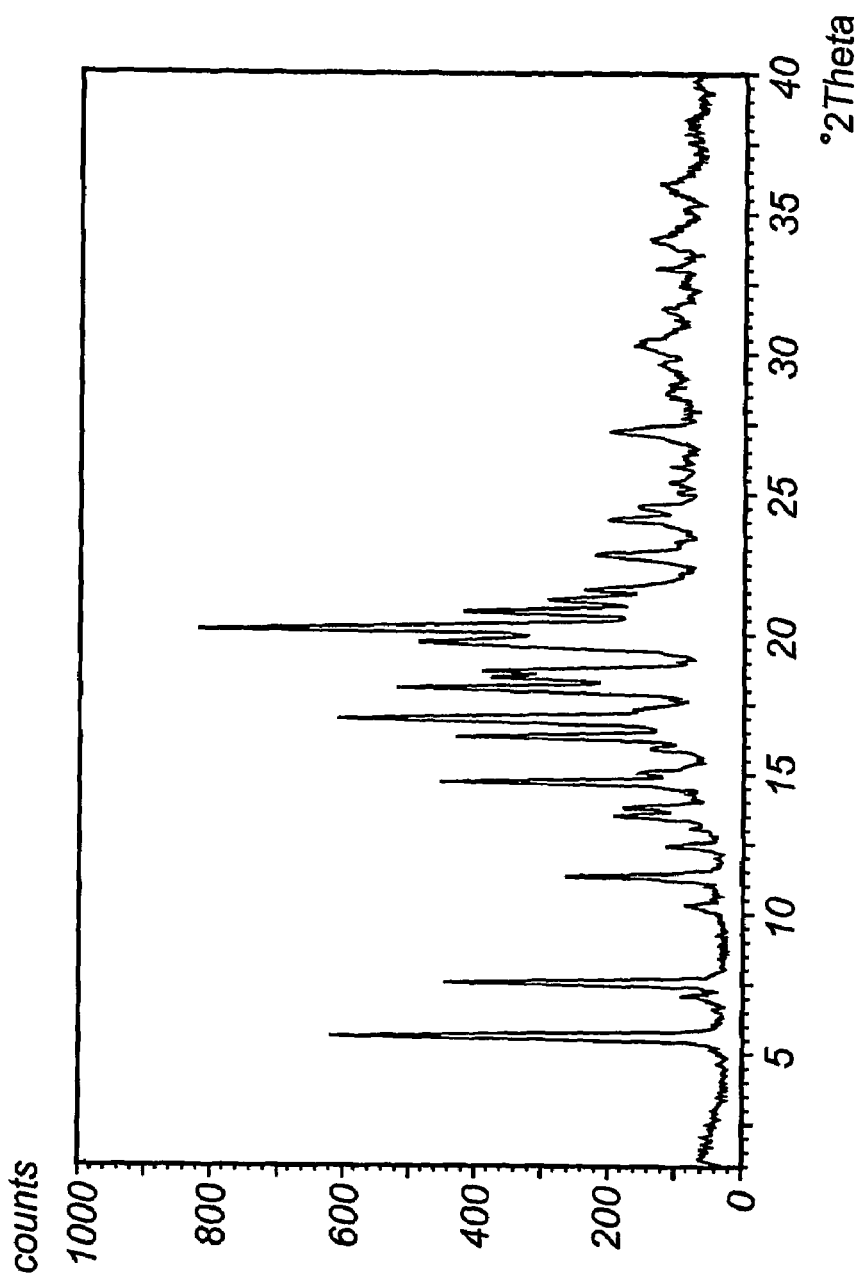
FIG. 1 is an X-ray powder diffractogram of the 1-adamantan ammonium salt of omeprazole.

The present invention refers to new adamantan ammonium salts having the following formula I including compounds Ia, Ib and Ic:

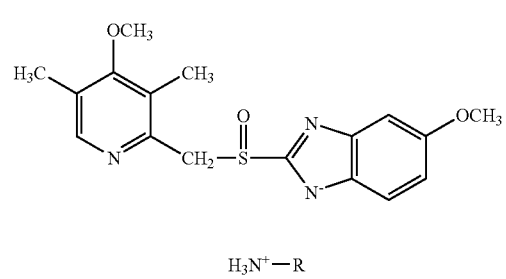

Formula Ia: adamantan ammonium salts of racemic omeprazole

Formula Ib: adamantan ammonium salts of the (S)-enantiomer of omeprazole

Formula Ic: adamantan ammonium salts of the (R)-enantiomer of omeprazole wherein R is defined as the adamantan group. The adamantan amine, $H_2N-R$, is selected from tricyclo[$3.3.1.1^{3,7}$]decan-1-amine and tricyclo[$3.3.1.13^{3,7}$]decan-2-amine.

The compounds of the invention may be prepared in the form of solvates, hydrates, and anhydrates.

The chemical name 5-methoxy-2-[[(4-methoxy-3,5-dimethyl-2-pyridinyl)-methyl]sulfinyl]-1H-benzimidazole adamantan ammonium salt as well as the chemical name (S)-5-methoxy-2-[[(4-methoxy-3,5-dimethyl-2-pyridinyl) methyl]sulfinyl]-1H-benzimidazole adamantan ammonium salt; the chemical name 5-methoxy-2-[[(4-methoxy-3,5-dimethyl-2-pyridinyl)-methyl]sulfinyl]-1H-benzimidazole 1-adamantan ammonium salt as well as the chemical name (S)-5-methoxy-2-[[(4-methoxy-3,5-dimethyl-2-pyridinyl) methyl]sulfinyl]-1H-benzimidazole 1-adamantan ammonium; and the chemical name 5-methoxy-2-[[(4-methoxy-3,5-dimethyl-2-pyridinyl)-methyl]sulfinyl]-1H-benzimidazole 2-adamantan ammonium salt as well as the chemical name (S)-5-methoxy-2-[[(4-methoxy-3,5-dimethyl-2-pyridinyl)methyl]sulfinyl]-1H-benzimidazole 2-adamantan ammonium salt does not necessarily mean that the methoxy group of the benzimidazole moieties is in the 5-position but may as well be in the 6-position, or there may be mixtures thereof.

In a further aspect, the present invention provides processes for the preparation of adamantan ammonium salts of omeprazole and of esomeprazole. It has surprisingly been found that adamantan ammonium salts of omeprazole and adamantan ammonium salts of the (R)- and (S)-enantiomers thereof may be obtained in a well-defined crystalline state. More specifically, the compounds adamantan ammonium salt of omeprazole and adamantan ammonium salt of esomeprazole according to the present invention are characterized by being crystalline with a well-defined structure.

Another embodiment of the invention is the 1-adamantan ammonium salt of omeprazole. This compound of the invention is characterized in providing an X-ray powder diffraction pattern, as in FIG. 1, exhibiting substantially the following d-values and intensities:

| d-value (Å) | Relative intensity |
|---|---|
| 15.6 | s |
| 11.6 | s |
| 8.6 | w |
| 7.8 | m |
| 7.1 | w |
| 6.6 | m |
| 6.4 | m |
| 6.0 | s |
| 5.9 | m |
| 5.6 | w |
| 5.4 | s |
| 5.2 | s |
| 4.90 | s |
| 4.87 | m |
| 4.80 | m |
| 4.74 | m |
| 4.49 | s |
| 4.46 | m |
| 4.40 | s |
| 4.26 | s |
| 4.18 | m |
| 4.11 | m |
| 3.90 | m |
| 3.70 | w |
| 3.63 | w |
| 3.28 | m |
| 2.95 | w |
| 2.63 | w |
| 2.50 | w |

The peaks, identified with d-values calculated from the Bragg formula and intensities, have been extracted from the diffractogram of the 1-adamantan ammonium salt of omeprazole. The relative intensities are less reliable and instead of numerical values, the relative intensities corresponding to the peaks are denoted being strong (s), medium (m), or weak (w).

In addition to the peaks indicated in the table the diffractogram contains a number of very weak peaks.

Another embodiment of the invention is the 1-adamantan ammonium salt of esomeprazole. This compound of the invention is characterized in providing an X-ray powder diffraction pattern, as in FIG. 2, exhibiting substantially the following d-values and intensities:

| d-value (Å) | Relative Intensity |
|---|---|
| 16.5 | w |
| 15.6 | w |
| 13.8 | w |
| 13.1 | w |
| 12.7 | w |
| 11.9 | w |
| 10.6 | s |
| 8.3 | w |
| 7.9 | w |
| 6.6 | w |
| 6.5 | m |
| 6.3 | w |
| 6.1 | m |
| 5.9 | w |
| 5.7 | w |
| 5.6 | m |
| 5.3 | m |
| 5.2 | m |
| 5.1 | s |
| 5.0 | m |
| 4.90 | w |
| 4.79 | w |
| 4.63 | m |
| 4.61 | m |
| 4.45 | m |
| 4.39 | s |
| 4.25 | m |
| 4.18 | m |
| 3.95 | w |
| 3.83 | w |
| 3.32 | w |
| 2.93 | w |
| 2.88 | w |
| 2.77 | w |
| 2.72 | w |
| 2.55 | w |

The peaks, identified with d-values calculated from the Bragg formula and intensities, have been extracted from the diffractogram of the 1-adamantan ammonium salt of esomeprazole.

The relative intensities are less reliable and instead of numerical values, the relative intensities corresponding to the peaks are denoted being strong (s), medium (m), or weak (w).

In addition to the peaks indicated in the table the diffractogram contains a number of very weak peaks.

Another embodiment of the invention is the 2-adamantan ammonium salt of esomeprazole. This compound of the invention is characterized in providing an X-ray powder diffraction pattern, as in FIG. 3, exhibiting substantially the following d-values and intensities:

| d-value (Å) | Relative Intensity |
|---|---|
| 15.8 | m |
| 11.1 | s |
| 7.9 | m |
| 7.8 | w |
| 7.0 | w (broad) |
| 6.3 | w |
| 6.1 | s |
| 5.9 | w |
| 5.7 | w |
| 5.5 | w |
| 5.3 | w |
| 5.2 | w |
| 5.0 | m |
| 4.93 | s |
| 4.82 | s |

-continued

| d-value (Å) | Relative Intensity |
| --- | --- |
| 4.66 | m |
| 4.39 | s (broad) |
| 4.27 | w |
| 4.19 | w |
| 4.12 | w |
| 3.96 | m |
| 3.77 | w |
| 3.58 | w |
| 3.53 | m |
| 3.49 | w |
| 3.28 | m (broad) |
| 3.21 | w |
| 3.14 | w |
| 3.05 | w |
| 2.98 | w |
| 2.97 | w |
| 2.93 | m |
| 2.87 | w |
| 2.83 | w |
| 2.78 | w |

The peaks, identified with d-values calculated from the Bragg formula and intensities, have been extracted from the diffractogram of the 2-adamantan ammonium salt of esomeprazole.

The relative intensities are less reliable and instead of numerical values, the relative intensities corresponding to the peaks are denoted being strong (s), medium (m), or weak (w).

In addition to the peaks indicated in the table the diffractogram contains a number of very weak peaks.

The relative intensities are derived from the diffractograms measured with variable slits. The XRPD distance values may vary in the range of ±2 on the last decimal place.

X-ray powder diffraction (XRPD) analysis was performed on samples of 1-adamantan ammonium salt of omeprazole, on samples of 1-adamantan ammonium salt of esomeprazole, and on samples of 2-adamantan ammonium salt of esomeprazole according to standard methods, for example, those described in Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; Bunn, C. W. (1948), Chemical Crystallography, Clarendon Press, London; or Klug, H. P. & Alexander, L. E. (1974), X-ray Diffraction Procedures, John Wiley and Sons, New York. X-ray analyses were performed using a Siemens D5000 diffractometer.

The compounds of the invention are characterized by the positions and intensities of the peaks in the X-ray powder diffractogram. Furthermore, the compounds of the invention could be characterized by $^1$H-NMR, IR, FRIR and Raman spectroscopy.

In a further aspect, the present invention provides processes for the preparation of adamantan ammonium salts of omeprazole and of esomeprazole, respectively. Suitable processes for the salt formation are temperature induced crystallisation, fast crystallisation at elevated temperature, slow crystallisation at room temperature, thermal recrystallisation, antisolvent induced crystallisation and crystallisation by evaporation.

In a further aspect, the present invention provides processes for the preparation of adamantan ammonium salts of omeprazole and of esomeprazole, which comprises the following steps: omeprazole or esomeprazole is either dissolved or formed in situ in a suitable solvent, such as acetonitril, ethyl acetate, tert-butyl methyl ether and methanol, or mixtures thereof. The adamantan amine is added during stirring. A precipitate of the salt compound is formed and the precipitate is separated by filtration. The obtained compound is washed with a solvent and the obtained crystals are dried.

Still a further aspect of the invention is that the novel compounds may be of interest as intermediates in the synthesis of other compounds such as magnesium salts of omeprazole and of esomeprazole, which are the pharmaceutically active components in products with the tradenames Losec® MUPS® and Nexium®. During the synthesis of the active component for Nexium® i.e. the magnesium salt of esomeprazole, a titanium catalyst may be used in the oxidation step prior to the salt formation steps. The synthesis usually proceeds with the formation of monovalent salt of esomeprazole by adding a monovalent hydroxide or alkoxide. This monovalent salt of esomeprazole, such as sodium or potassium salt, is thereafter converted to the magnesium salt. Insoluble inorganic titanium salts, such as titanium oxid, are being formed when strong bases such as sodium or potassium alkoxides are being added to a solution of titanium catalysts. Using adamantan amine as a salt forming agent rather than using a sodium- or potassium-containing base avoids the risk of inorganic titanium salts being co-precipitated with the desired salt. Even, if the titanium-catalyst may react with the adamantan amine, a soluble complex of the adamantane amine and titanium may be formed, which may stay in the solution while filtering off the desired adamantane ammonium salt of the benzimidazole compound.

Solutions containing the dissolved and ionised alkylammonium salt of omeprazole or alkylammonium salt of esomeprazole have a lower pH than corresponding solutions made from the previously known sodium and potassium salts of omeprazole and of esomeprazole. Less basic solutions are advantageous for intravenous administration.

The exemplified adamantan ammonium salts of omeprazole and esomeprazole, respectively, are in crystalline forms. They exhibit advantageous properties, such as convenient handling as well as chemical and solid-state stability. The products obtained according to the present invention are well-defined crystalline products. Such crystalline products give an easily processability during the manufacture of suitable dosage forms. A crystalline product is easy to handle during milling, filtering and tableting. The procedures have high reproducibility. Also, the stability is improved when a well-defined crystalline form of the compound is obtained. These properties are of great value considering dosage forms such as e.g. tablets.

These active substances are useful for inhibiting gastric acid secretion in mammals and man. In a more general sense, they may be used for prevention and treatment of gastric acid related diseases in mammals and man, including e.g. reflux esophagitis, gastritis, duodenitis, gastric ulcer and duodenal ulcer. Furthermore, they may be used for treatment of other gastrointestinal disorders where gastric acid inhibitory effect is desirable e.g. in patients on NSAID (nonsteroidal anti-inflammatory drug) therapy, in patients with Non Ulcer Dyspepsia, in patients with symptomatic and non-symptomatic gastro-esophageal reflux disease, and in patients with gastrinomas. They may also be used in patients in intensive care situations, in patients with acute upper gastrointestinal bleeding, pre- and postoperatively to prevent acid aspiration of gastric acid and to prevent and treat stress ulceration. Further, they may be useful for prevention and treatment of irritable bowel syndrome (IBS), inflammatory bowel disease (IBD), ulcerative colitis and Crohn's disease, asthma, laryngitis, Barret's syndrome, sleep apnea, sleep disturbance, psoriasis as well as being useful for prevention and treatment of *Helicobacter* infections and diseases related to the above conditions.

For the avoidance of doubt, by "treatment" is meant to include the therapeutic treatment as well as the prophylaxis, of a condition.

Any suitable route of administration may be employed for providing the patient with an effective dosage of the adamantan ammonium salt of omeprazole or esomeprazole, according to the invention. For example, peroral or parenteral formulations and the like may be employed. Dosage forms include capsules, tablets, dispersions, suspensions and the like.

It is further provided a pharmaceutical composition comprising the compounds according to the invention, as active ingredient, in association with a pharmaceutically acceptable carrier, diluent or excipient and optionally other therapeutic ingredients. Compositions comprising other therapeutic ingredients are especially of interest in the treatment of *Helicobacter* infections. The invention also provides the use of the compounds in the manufacture of a medicament for use in the treatment of a gastric-acid related condition and a method of treating a gastric-acid related condition which method comprises administering to a subject suffering from said condition a therapeutically effective amount of the compounds according to the invention.

The composition of the invention includes compositions suitable for peroral or parenteral administration. The most preferred route is the oral route. The compositions may be conveniently presented in unit dosage forms, and prepared by any methods known in the art of pharmacy.

In the practice of the invention, the most suitable route of administration as well as the magnitude of a therapeutic dose of the compounds according to the invention in any case will depend on the nature and severity of the disease to be treated. The dose, and dose frequency, may also vary according to the age, body weight and response of the individual patient. Special requirements may be needed for patients having Zollinger-Ellison syndrome, such as a need for higher doses than the average patient. Children and patients with liver diseases generally will benefit from doses that are somewhat lower than average. Thus, in some conditions it may be necessary to use doses outside the ranges stated below, for example long-term treatments may request lower dosage. Such higher and lower doses are within the scope of the present invention. Such daily doses may vary between 5 mg to 300 mg.

In general, a suitable oral dosage form of the compound of the invention may cover a dose range from 5 mg to 300 mg total daily dose, administered in one single dose or equally divided doses. A preferred dosage range is from 10 mg to 80 mg.

The compound of the invention may be combined as the active component in intimate admixture with a pharmaceutical carrier according to conventional techniques, such as the oral formulations described in WO 96/01623 and EP 0 247 983, the disclosures of which are hereby as a whole included by reference.

Combination preparations comprising the compounds of the invention and other active ingredients may also be used. Examples of such active ingredients include, but are not limited to anti-bacterial compounds, non-steroidal anti-inflammatory agents (including acetylsalicylic acid (ASA), antacid agents, alginates, prokinetic agents, histamine $H_2$-receptor antagonists, bisfosfonates, and GABAb agonists such as baclofen and those is disclosed in WO 01/42252 and WO 01/41743.

The examples below will further illustrate the preparation of the compound of the invention, according to different process routes and including new intermediates. These examples are not intended to limit the scope if the invention as defined hereinabove or as claimed below.

EXAMPLES

Example 1

5-methoxy-2-[[(4-methoxy-3,5-dimethyl-2-pyridinyl)-methyl]sulfinyl]-1H-benzimidazole 1-adamantan ammonium salt Omeprazole (1.0 g, 2.9 mmol) was dissolved in acetonitril (10 ml) and methanol (2 ml) at 40-50° C. 1-adamantan amine (0.86 g, 5.7 mmol) was added and the mixture was then cooled to room temperature. At these conditions, a slurry was achieved. The slurry was stirred for additional two hours whereupon the precipitate was filtered off, washed with acetonitrile, and dried. 1 g (73%) of the title compound was obtained.

$^1$H-NMR (400 MHz, $CD_2C_2$): 1.5 (bs, 18H), 2.12 (s, 3H), 2.17 (s, 3H), 3.63 (s, 3H), 3.77 (s, 3H), 4.49 (d, 1H), 4.65 (d, 1H), 6.84-6.91 (dd, 1H), 6.99 (bs, 1H), 7.47 (m, 1H), 8.14 (s, 1H)

The prepared compound was analysed by XRPD resulting in the diffractogram shown in FIG. 1.

Example 2

(S)-5-methoxy-2-[[(4-methoxy-3,5-dimethyl-2-pyridinyl)-methyl]sulfinyl]-1H-benzimidazole 1-adamantan ammonium salt Esomeprazole (1.0 g, 2.9 mmol) was dissolved in acetonitril (20 ml) at room temperature. 1-Adamantan amine (0.86 g, 5.7 mmol) was added to the solution whereupon a white solid precipitated. The reaction slurry was stirred at room temperature for additional two hours. The formed precipitate was filtered off, washed with acetonitril (10 ml), and dried. 1.13 g (83%) of the title compound was obtained.

$^1$H-NMR (400 MHz, $CD_2Cl_2$): 1.48 (bs, 18H), 2.14 (s, 3H), 2.18 (s, 3H), 3.66 (s, 3H), 3.78 (s, 3H), 4.46 (d, 1H), 4.66 (d, 1H), 6.88 (d, 1H), 6.95 (m, 1H), 7.52 (d, 1H), 8.15 (s, 1H)

Figure 2:
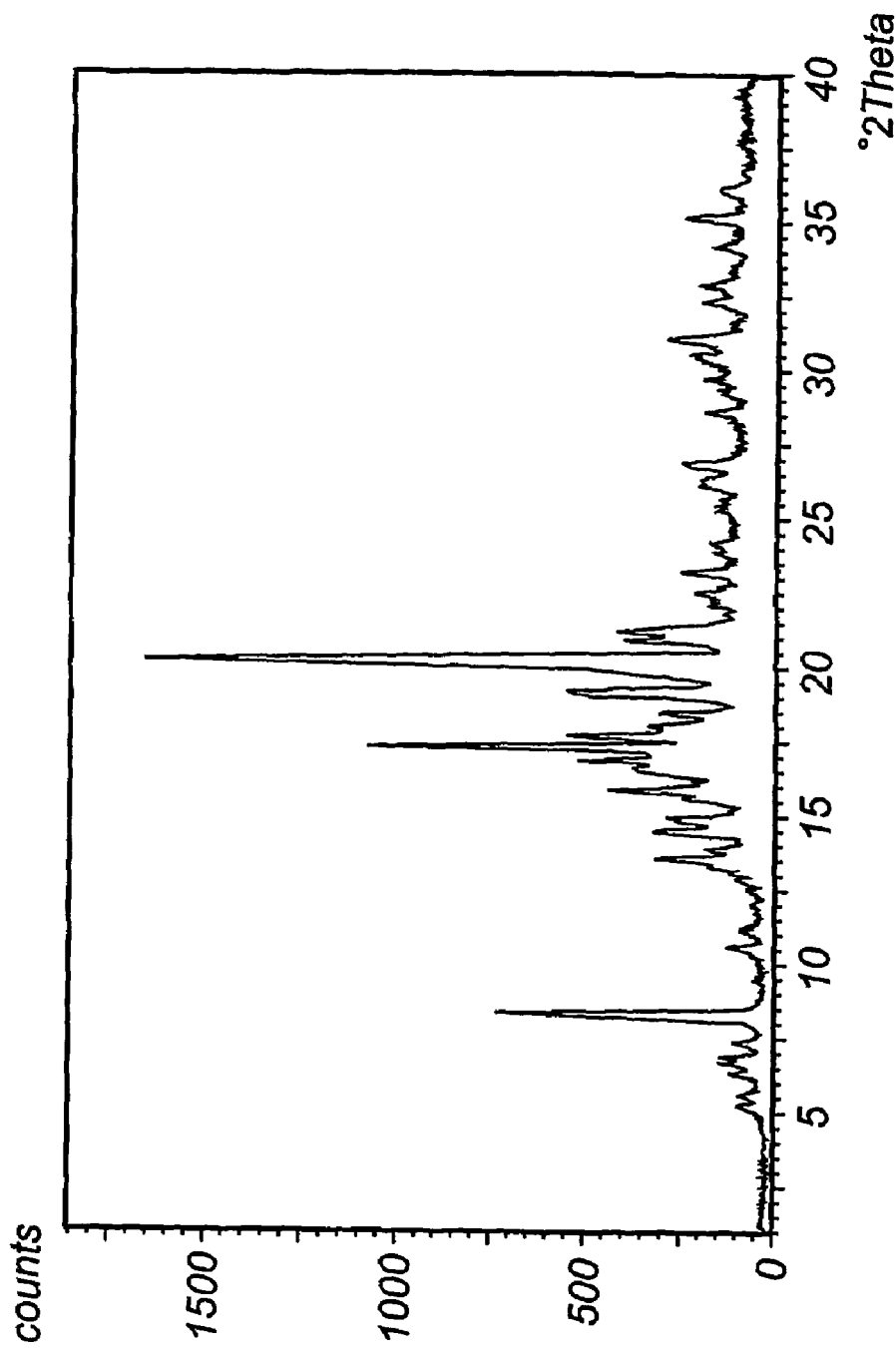
FIG. 2 is an X-ray powder diffractogram of the 1-adamantan ammonium salt of esomeprazole.

The prepared compound was analysed by XRPD resulting in the diffractogram shown in FIG. 2.

Example 3

(S)-5-methoxy-2-[[(4-methoxy-3,5-dimethyl-2-pyridinyl)-methyl]sulfinyl]-1H-benzimidazole 2-adamantan ammonium salt Esomeprazole (0.5 g, 1.4 mmol) was dissolved in a solution of 2-Adamantanamine (0.44 g, 2.9 mmol) and ethyl acetate (10 ml). The obtained solution was concentrated to about 4 ml and acetonitrile (10 ml) was added. The resulting mixture was concentrated once more to about half, whereupon a white solid started to precipitate. The reaction slurry was stirred at room temperature over night. The precipitated product was filtered off and washed with acetonitrile. 0.1 g of the title compound was obtained.

¹H-NMR (400 MHz, CD₃OD): 1.64 (d, 2H), 1.77-1.88 (m, 8H), 1.93 (d, 2H), 2.02 (d, 2H), 2.16 (s, 3H), 2.25 (s, 3H), 3.10 (bs, 1H), 3.70 (s, 3H), 3.86 (s, 3H), 4.69 (d, 1H), 4.84 (d, 1H), 6.92 (dd, 1H), 7.11 (d, 1H), 7.52 (d, 1H), 8.15 (s, 1H)

Figure 3:
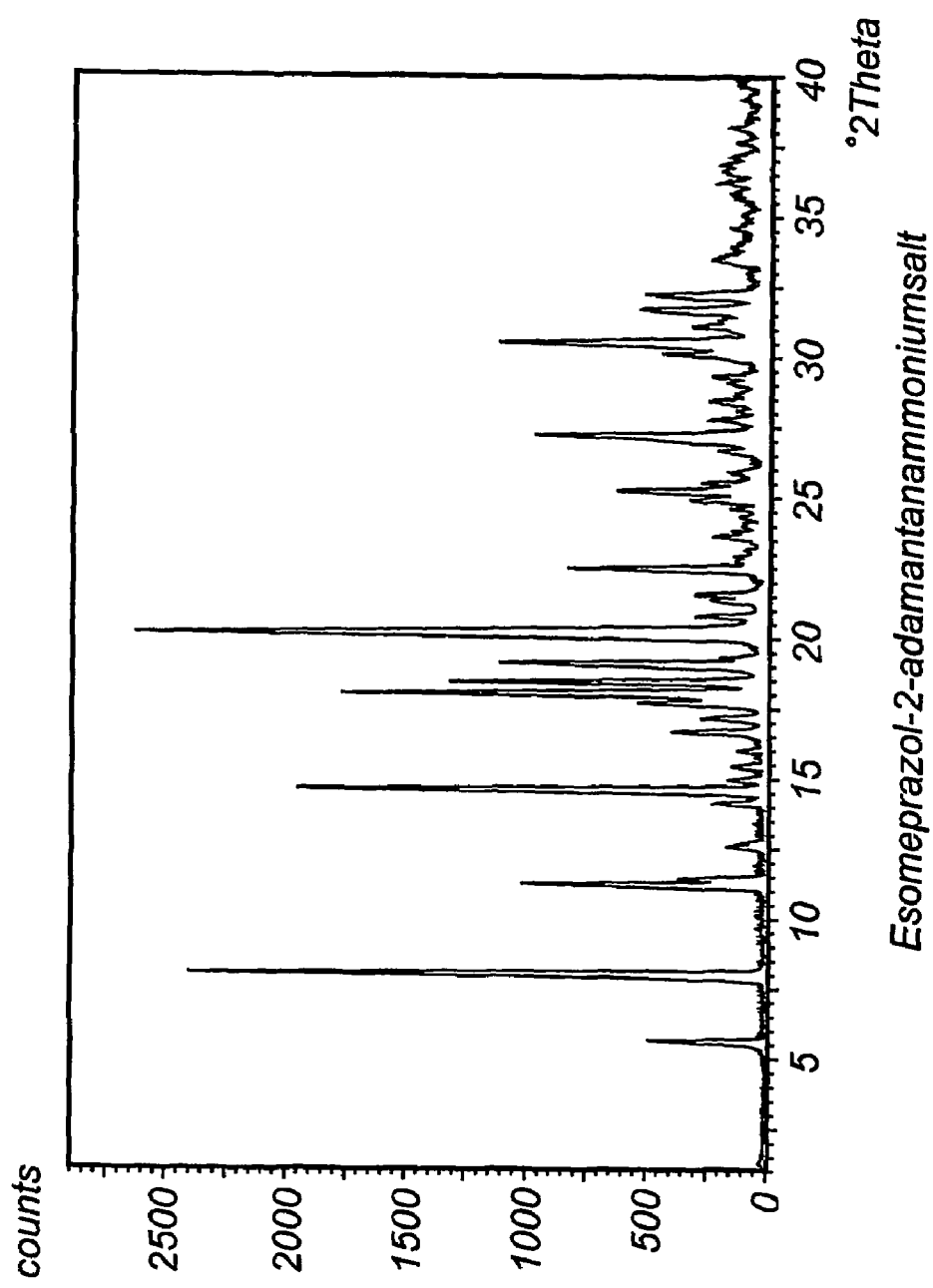
FIG. 3 is an X-ray powder diffractogram of the 2-adamantan ammonium salt of esomeprazole.

The prepared compound was analysed by XRPD resulting in the diffractogram shown in FIG. 3.

The invention claimed is:

1. An adamantan ammonium salt of 5-methoxy-2-[[(4-methoxy-3,5-dimethyl-2-pyridinyl)-methyl]sulfinyl]-1H-benzimidazole (omeprazole) or (S)-5-methoxy-2-[[(4-methoxy-3,5-dimethyl-2-pyridinyl)-methyl]sulfinyl]-1H-benzimidazole (esomeprazole).

2. The adamantan ammonium salt according to claim 1, wherein the salt is a 1-adamantan ammonium salt of omeprazole.

3. The adamantan ammonium salt according to claim 1, wherein the salt is a 1-adamantan ammonium salt of esomeprazole.

4. The adamantan ammonium salt according to claim 1, wherein the salt is a 2-adamantan ammonium salt of omeprazole.

5. The adamantan ammonium salt according to claim 1, wherein the salt is a 2-adamantan ammonium salt of esomeprazole.

6. The adamantan ammonium salt according to claim 1, wherein the salt is crystalline.

7. A process for the preparation of the adamantan ammonium salt according to claim 1, wherein the process comprises the steps of:

a) dissolving omeprazole or esomeprazole in an organic solvent;
b) adding an adamantan amine and precipitating the desired salt; and
c) isolating and drying the obtained salt.

8. The process according to claim 7, wherein the organic solvent is selected from the group consisting of acetonitrile, ethyl acetate, tert-butyl methyl ether, methanol, and mixtures thereof.

9. The process according to claim 7, wherein the organic solvent is selected from the group consisting of acetonitrile, ethyl acetate, methanol, and mixtures thereof.

10. The process according to claim 7, wherein the obtained salt is an adamantan ammonium salt of omeprazole.

11. The process according to claim 7, wherein the obtained salt is an adamantan ammonium salt of esomeprazole.

12. A pharmaceutical composition comprising the adamantan ammonium salt of omeprazole or esomeprazole according to any one of claims 1 to 6 as active ingredient and one or more pharmaceutically acceptable excipients.

13. A method for inhibiting gastric acid secretion, which method comprises administering a therapeutically effective amount of the adamantan ammonium salt of omeprazole or esomeprazole according to any one of claims 1 to 6 to a patient in need thereof.

* * * * *